(12) United States Patent
Sato et al.

(10) Patent No.: US 9,231,251 B2
(45) Date of Patent: Jan. 5, 2016

(54) ELECTRODE ACTIVE MATERIAL AND SECONDARY BATTERY

(71) Applicants: Murata Manufacturing Co., Ltd., Nagaokakyo-shi, Kyoto-fu (JP); Nard Institute, Ltd., Amagasaki-shi, Hyogo (JP)

(72) Inventors: Masaharu Sato, Nagaokakyo (JP); Toyonari Sugimoto, Sakai (JP); Takayuki Kubota, Amagasaki (JP); Takayuki Matsunaga, Amagasaki (JP)

(73) Assignees: MURATA MANUFACTURING CO., LTD., Nagaokakyo-Shi, Kyoto-Fu (JP); NARD INSTITUTE, LTD., Amagasaki-Shi, Hyogo (JP)

(*) Notice: Subject to any disclaimer, the term of this patent is extended or adjusted under 35 U.S.C. 154(b) by 266 days.

(21) Appl. No.: 13/852,468

(22) Filed: Mar. 28, 2013

(65) Prior Publication Data
US 2013/0216909 A1   Aug. 22, 2013

Related U.S. Application Data

(63) Continuation of application No. PCT/JP2011/072398, filed on Sep. 29, 2011.

(30) Foreign Application Priority Data

Sep. 30, 2010   (JP) .................. 2010-221851

(51) Int. Cl.
*H01M 4/60* (2006.01)
*C07D 487/14* (2006.01)
*H01M 10/0525* (2010.01)

(52) U.S. Cl.
CPC .............. *H01M 4/60* (2013.01); *C07D 487/14* (2013.01); *H01M 4/604* (2013.01); *H01M 4/608* (2013.01); *H01M 10/0525* (2013.01)

(58) Field of Classification Search
CPC ........................................................ H01M 4/60
USPC ........................................................ 429/213
See application file for complete search history.

(56) References Cited

U.S. PATENT DOCUMENTS

| | | | |
|---|---|---|---|
| 6,678,150 | B2 | 1/2004 | Nakagawa et al. |
| 7,018,738 | B2 | 3/2006 | Morioka et al. |
| 7,476,465 | B2 | 1/2009 | Morioka et al. |

FOREIGN PATENT DOCUMENTS

| | | | |
|---|---|---|---|
| JP | 2003115297 A | 4/2003 |
| JP | 2003242980 A | 8/2003 |
| JP | 2003257431 A | 9/2003 |

(Continued)

OTHER PUBLICATIONS

Joaquin Geng; Stéven Renault; Philippe Poizot and Franck Dolhem. "Search for greener Li-ion batteries: an alternative offered by organic electroactive materials", Proc. SPIE 8035, Energy Harvesting and Storage: Materials, Devices, and Applications II, 803504 (May 16, 2011); doi:10.1117/12.883244; http://dx.doi.org/10.1117/12.883244.*

(Continued)

*Primary Examiner* — Kenneth Douyette
*Assistant Examiner* — James Lee
(74) *Attorney, Agent, or Firm* — Arent Fox LLP

(57) ABSTRACT

An electrode active material is based on an organic compound containing in the structural unit thereof a pyrazine structure bound to cycloalkane. The electrode active material and a secondary battery containing it have large energy density, outputting high power, and having excellent cycle characteristics with little reduction in capacity even after repetition of charging and discharging.

19 Claims, 1 Drawing Sheet

(56) References Cited

FOREIGN PATENT DOCUMENTS

| JP | 2004-207249 A | 7/2004 |
| JP | 2004192829 A | 7/2004 |

OTHER PUBLICATIONS

International Search Report and Written Opinion, issued in PCT/JP2011/072398, mailed Jan. 10, 2012.

* cited by examiner

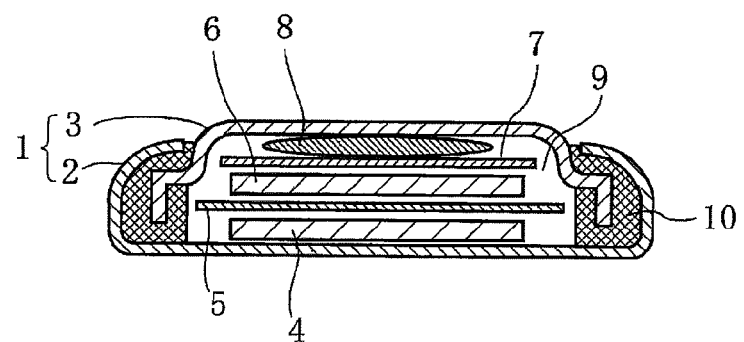

ELECTRODE ACTIVE MATERIAL AND SECONDARY BATTERY

This is a continuation of application Ser. No. PCT/JP2011/072398, filed Sep. 29, 2011, the entire contents of which is incorporated herein by reference.

TECHNICAL FIELD

The present invention relates to an electrode active material and a secondary battery, and more specifically, to an electrode active material including an organic compound, and a secondary battery that is repeatedly charged and discharged utilizing the battery electrode reaction of the electrode active material.

BACKGROUND ART

As the market of portable electronic devices such as cellular phones, notebook personal computers and digital cameras expands, secondary batteries having high energy density and long life time functioning as cordless power sources for these electronic devices are eagerly demanded.

For responding to such a demand, a secondary battery having alkali metal ion such as lithium ion as a charge carrier, and utilizing the electrochemical reaction associated with donation and reception of electric charge has been developed. In particular, a lithium ion secondary battery having large energy density becomes widely used today.

Of constituents of a secondary battery, an electrode active material is a substance that directly contributes to the battery electrode reaction including charging and discharging, and plays the central role in the secondary battery. The battery electrode reaction is a reaction occurring in association with donation and reception of an electron when a voltage is applied on the electrode active material that is electrically connected with an electrode disposed in an electrolyte, and proceeds at the time of charging or discharging of the battery. Therefore, as described above, the electrode active material plays the central role in the secondary battery in terms of the system.

In the foregoing lithium ion secondary battery, which uses a lithium-containing transition metal oxide as a cathode active material and a carbon material as an anode active material, charging or discharging is achieved by utilizing the insertion and elimination of lithium ions to/from these electrode active materials.

However, the foregoing lithium ion secondary battery faces the problem that the speed of charging or discharging is limited because movement of lithium ion in the cathode is rate-limiting. In other words, the moving speed of lithium ion in the transition metal oxide in the cathode is lower than those in the electrolyte and the anode, in the aforementioned lithium ion secondary battery, so that the battery reaction speed in the cathode is rate-limiting, to limit the charging or discharging speed, and as a result, realization of high power and reduction in the charging time are limited.

A secondary battery including an organic compound as a cathode active material is proposed in recent years for solving such a problem. Research and development for secondary batteries, including an organic radical compound of such organic compounds has been actively made.

For example, Patent Document 1 proposes an active material for a secondary battery which includes a nitroxyl radical compound, an oxy radical compound, and a nitrogen radical compound having a radical on a nitrogen atom.

Patent Document 1 describes an example in which a highly-stable nitroxyl radical or the like is used as a radical, and demonstrates that when a secondary battery produced, for example, by using an electrode layer containing a nitronyl nitroxide compound as a cathode and a lithium-bonded copper foil as an anode, is repeatedly charged and discharged, the charging and discharging is possible for greater than or equal to 10 cycles.

Patent Document 2 proposes an electrode containing a compound having a diazine N,N'-dioxide structure as an electrode active material, and Patent Document 3 proposes an electrode active material containing an oligomer or polymer compound having a diazine N,N'-dioxide structure in its side chain.

In these Patent Documents 2 and 3, a diazine N,N'-dioxide compound or a polymer compound having a diazine N,N'-dioxide structure in its side chain functions as an electrode active material in the electrode, and in the discharging reaction of the electrode reaction, or in the charging and discharging reactions, it is contained in the electrode as a reaction starting substance, a product, or an intermediate product. Five different conditions can be obtained by donation and reception of an electron in the oxidation-reduction reaction, and this implies the possibility of multi-electron reaction in which greater than or equal to two electrons are involved in the reaction.

PATENT DOCUMENT CITATION LIST

PTD 1: Japanese Patent Laying-Open No. 2004-207249
PTD 2: Japanese Patent Laying-Open No. 2003-115297
PTD 3: Japanese Patent Laying-Open No. 2003-242980

SUMMARY OF INVENTION

Technical Problem

The charging and discharging reaction in Patent Document 1 is limited to a one-electron reaction in which only one electron is involved although an organic radical compound such as a nitroxyl radical compound is used as the electrode active material. That is, in the case of an organic radical compound and a multi-electron reaction in which greater than or equal to two electrons are involved is caused to occur, the radical lacks the stability and can be decomposed, so that the radical disappears and the reversibility of charging and discharging reaction is lost. Accordingly, there is no choice in the organic radical compound in Patent Document 1 but to limit the reaction to one-electron reaction, and it is difficult to realize multi-electron reaction with which high capacity is expected.

In Patent Documents 2 and 3, stability in the oxidation state and the reduction state is not sufficient although multi-electron reaction by greater than or equal to two electrons is conceivable, so that practical use has not been realized yet.

As described above, even when an organic radical compound or a compound having a diazine structure is used as an electrode active material in conventional secondary batteries as shown in Patent Documents 1 to 3, it is difficult to realize both increased capacity by multi-electron reaction and stability to the charging and discharging cycles. Therefore, an electrode active material having sufficiently large energy density, realizing high output, having excellent cycle characteristics, and having long service life has not been realized in conventional secondary batteries.

The present invention was devised in consideration of such circumstances, and it is an object of the present invention to provide an electrode active material and a secondary battery having high energy density, outputting high power, and having excellent cycle characteristics with little reduction in capacity even after repetition of charging and discharging.

Solution to Problem

The present inventors made diligent studies for obtaining an organic compound that can be used as an active material of a secondary battery, and found that an organic compound containing a pyrazine structure bound to a cycloalkane in the structural unit thereof is able to have a multi-electron reaction, has excellent stability in oxidation-reduction reaction, and is capable of charging a large quantity of electricity with a small molecular weight.

The present invention was devised based on these findings, and the electrode active material according to the present invention is an electrode active material used as an active material in a secondary battery that is repeatedly charged and discharged by battery electrode reaction, and is featured by being based on an organic compound containing a pyrazine structure bound to cycloalkane in the structural unit thereof.

In the electrode active material of the present invention, the organic compound is preferably represented by the following general chemical formula 4:

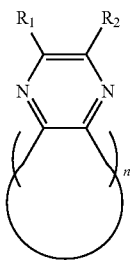

(wherein, $R_1$ and $R_2$ each represent at least one of a hydrogen atom, a substituted or unsubstituted $C_1$-$C_{50}$ alkyl group, an aryl group, an aralkyl group, a cycloalkyl group, an alkoxyl group, an alkenyl group, an aryloxy group, an arylamino group, an alkylamino group, a thioaryl group, a thioalkyl group, a heterocyclic group, a formyl group, a silyl group, a boryl group, a stannyl group, a cyano group, a nitro group, a nitroso group, a carboxyl group, an alkoxycarbonyl group and a halogen atom, and $R_1$ and $R_2$ may be identical to each other, and may be bound to each other to form a saturated or unsaturated ring, and n is an integer of 1 to 50).

Further, in the electrode active material of the present invention, the organic compound is preferably represented by the general chemical formula 5:

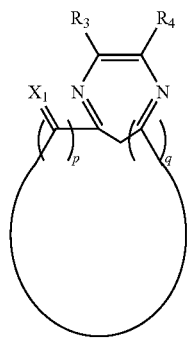

wherein, $R_3$ and $R_4$ each represent at least one of a hydrogen atom, a substituted or unsubstituted $C_1$-$C_{50}$ alkyl group, an aryl group, an aralkyl group, a cycloalkyl group, an alkoxyl group, an alkenyl group, an aryloxy group, an arylamino group, an alkylamino group, a thioaryl group, a thioalkyl group, a heterocyclic group, a formyl group, a silyl group, a boryl group, a stannyl group, a cyano group, a nitro group, a nitroso group, a carboxyl group, an alkoxycarbonyl group and a halogen atom, and $R_3$ and $R_4$ may be identical to each other. $X_1$ represents $CH_2$, $CF_2$, O, S, Se, N—R', P—R', and As—R' where R' represents at least any one of a hydrogen atom, a substituted or unsubstituted $C_1$-$C_{50}$ alkyl group, an aryl group, an aralkyl group, a cycloalkyl group, an alkoxyl group, an alkenyl group, an aryloxy group, an arylamino group, an alkylamino group, a thioaryl group, a thioalkyl group, a heterocyclic group, a silyl group, a boryl group, a stannyl group, a cyano group, a nitro group, a nitroso group, and a halogen atom, and $R_3$, $R_4$ and $X_1$ may be bound to each other to form a saturated or unsaturated ring. p and q each are an integer of 1 to 50, and may be identical to each other.

Further, in the electrode active material of the present invention, the organic compound is preferably represented by the general chemical formula 6:

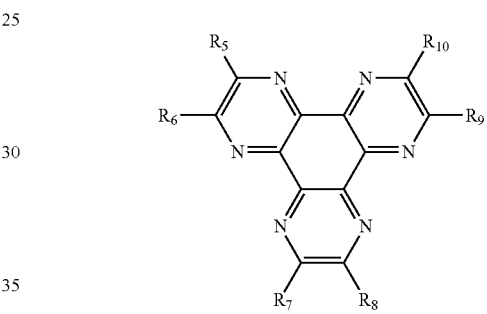

(wherein, $R_5$ to $R_{10}$ each represent at least any one of a hydrogen atom, a substituted or unsubstituted C1-C50 alkyl group, an aryl group, an aralkyl group, a cycloalkyl group, an alkoxyl group, an alkenyl group, an aryloxy group, an arylamino group, an alkylamino group, a thioaryl group, a thioalkyl group, a heterocyclic group, a formyl group, a silyl group, a boryl group, a stannyl group, a cyano group, a nitro group, a nitroso group, a carboxyl group, an alkoxycarbonyl group and a halogen atom, and $R_5$ to $R_{10}$ may be identical to each other, and may be bound to each other to form a saturated or unsaturated ring.

A secondary battery according to the present invention is featured in that any one of the electrode active materials described above is included in any one of a reaction starting substance, a product and an intermediate product at least in discharging reaction of battery electrode reaction.

The secondary battery according to the present invention is featured by having a cathode, an anode, and an electrolyte, the cathode having the electrode active material.

Advantageous Effects of Invention

Since the electrode active material of the present invention is based on an organic compound containing a pyrazine structure bound to cycloalkane in the structural unit thereof, it is possible to obtain an electrode active material that is able to have a multi-electron reaction, has excellent stability to an oxidation-reduction reaction, has a high capacity density with a small molecular weight, and has excellent cycle characteristics.

Further, since the electrode active material according to the secondary battery of the present invention is included in a reaction starting substance, a product and an intermediate product at least in discharging reaction of battery electrode reaction, it is possible to obtain a secondary battery capable of realizing both the multi-electron reaction and stability to the charging and discharging cycles, having large energy density, outputting high power, and having excellent cycle characteristics and long service life with little reduction in capacity even after repetition of charging and discharging.

BRIEF DESCRIPTION OF DRAWINGS

FIG. 1 is a section view of one embodiment of a coin-shaped battery as a secondary battery according to the present invention.

DESCRIPTION OF EMBODIMENTS

Next, embodiments of the present invention will be described in detail.

The electrode active material of the present invention is based on an organic compound containing a pyrazine structure bound to cycloalkane in the structural unit thereof. Therefore, it is possible to obtain a secondary battery capable of having multi-electron reaction by greater than or equal to two electrons, improving stability of oxidation-reduction reaction, and having high energy density and excellent stability.

The organic compound having a pyrazine structure bound to cycloalkane may be concretely represented by general formula (1):

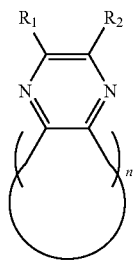

(1)

$R_1$ and $R_2$ each represent at least any one of a hydrogen atom, a substituted or unsubstituted C1-C50 alkyl group, an aryl group, an aralkyl group, a cycloalkyl group, an alkoxyl group, an alkenyl group, an aryloxy group, an arylamino group, an alkylamino group, a thioaryl group, a thioalkyl group, a heterocyclic group, a formyl group, a silyl group, a boryl group, a stannyl group, a cyano group, a nitro group, a nitroso group, a carboxyl group, an alkoxycarbonyl group and a halogen atom; $R_1$ and $R_2$ may be identical to each other, and may be bound to each other to form a saturated or unsaturated ring; and n is an integer of 1 to 50. n is designated between 1 and 50 because when n exceeds 50, the molecular weight excessively increases, and decrease in capacity density may be caused.

Further, as the organic compound having a pyrazine structure bound to cycloalkane, an organic compound having a cyclic "one" structure (including monoone, dione and derivatives thereof) as shown in the following general formula (2) may be recited.

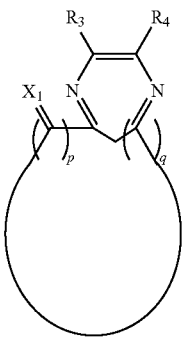

(2)

$R_3$ and $R_4$ each represent at least any one of a hydrogen atom, a substituted or unsubstituted C1-C50 alkyl group, an aryl group, an aralkyl group, a cycloalkyl group, an alkoxyl group, an alkenyl group, an aryloxy group, an arylamino group, an alkylamino group, a thioaryl group, a thioalkyl group, a heterocyclic group, a formyl group, a silyl group, a boryl group, a stannyl group, a cyano group, a nitro group, a nitroso group, a carboxyl group, an alkoxycarbonyl group and a halogen atom, and $R_3$ and $R_4$ may be identical to each other. $X_1$ represents $CH_2$, $CF_2$, O, S, Se, N—R', P—R', and As—R' (R' represents at least any one of a hydrogen atom, a substituted or unsubstituted $C_1$-$C_{50}$ alkyl group, an aryl group, an aralkyl group, a cycloalkyl group, an alkoxyl group, an alkenyl group, an aryloxy group, an arylamino group, an alkylamino group, a thioaryl group, a thioalkyl group, a heterocyclic group, a silyl group, a boryl group, a stannyl group, a cyano group, a nitro group, a nitroso group, and a halogen atom), and $R_3$, $R_4$ and $X_1$ may be bound to each other to form a saturated or unsaturated ring. p and q each are an integer of 1 to 50, and may be identical to each other. p and q are designated between 1 and 50 because when p and q exceed 50, the molecular weight excessively increases, and decrease in capacity density may be caused.

Further, of the above-mentioned organic compounds included in the category of general formula (1), an organic compound represented by general formula (3) below wherein cycloalkane is formed by cyclohexane is particularly preferred.

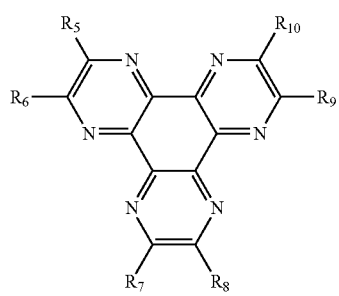

(3)

$R_5$ to $R_{10}$ each represent at least any one of a hydrogen atom, a substituted or unsubstituted $C_1$-$C_{50}$ alkyl group, an aryl group, an aralkyl group, a cycloalkyl group, an alkoxyl group, an alkenyl group, an aryloxy group, an arylamino group, an alkylamino group, a thioaryl group, a thioalkyl group, a heterocyclic group, a formyl group, a silyl group, a boryl group, a stannyl group, a cyano group, a nitro group, a nitroso group, a carboxyl group, an alkoxycarbonyl group and a halogen atom. $R_5$ to $R_{10}$ may be identical to each other, and may be bound to each other to form a saturated or unsaturated ring.

Although substituents $R_1$ to $R_{10}$ recited in the above general formulas (1) to (3) are not limited as far as they belong to respective categories, they are preferably selected within the range of a molecular weight of up to about 250 because as the molecular weight increases, the charge amount that can be accumulated per unit mass of the active material decreases.

As an organic compound belonging to the category of general formula (3), organic compounds represented, for example by chemical formulas (4A) to (4N) can be recited.

(4A)
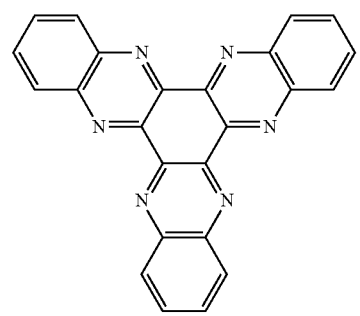

(4B)
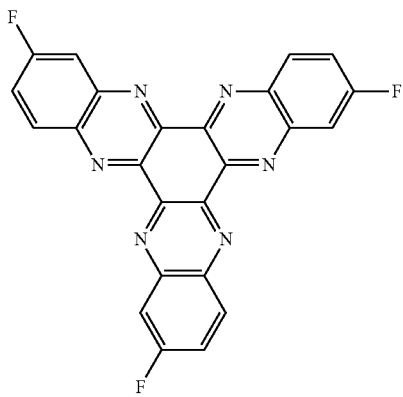

(4C)
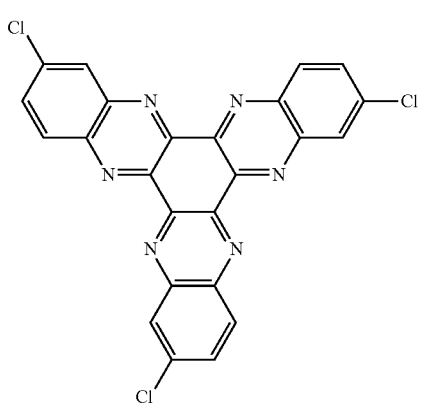

(4D)
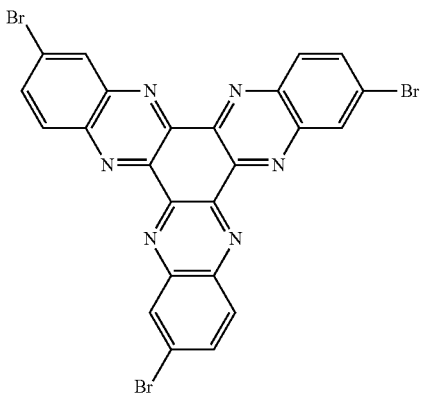

(4E)
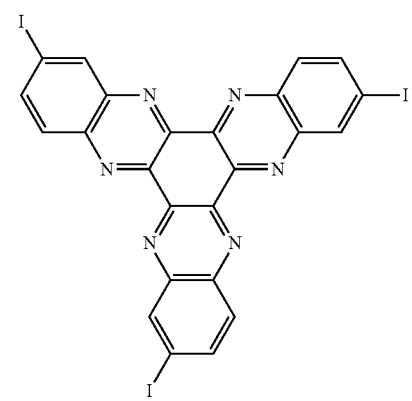

(4F)
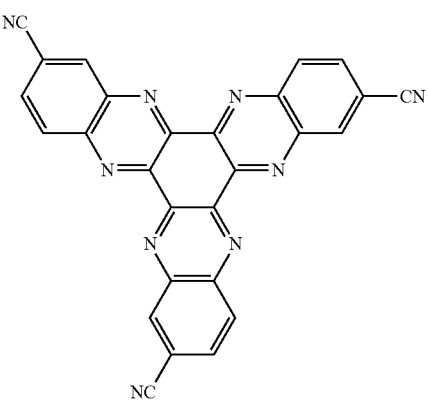

(4G)
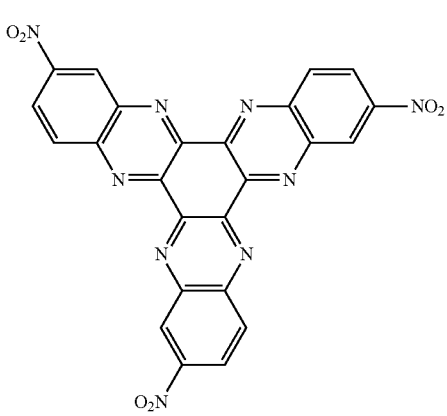

-continued (4H)
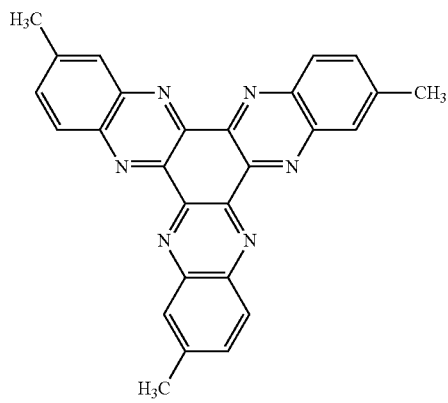

(4I)
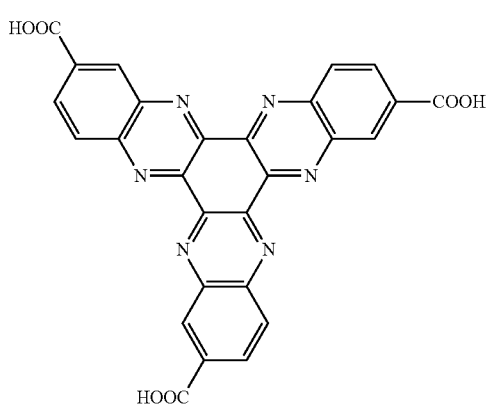

(4J)
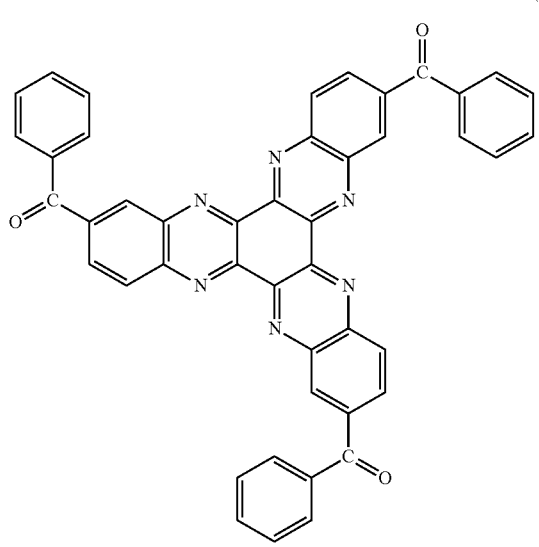

(4K)
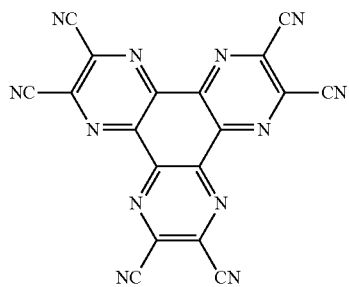

(4L)
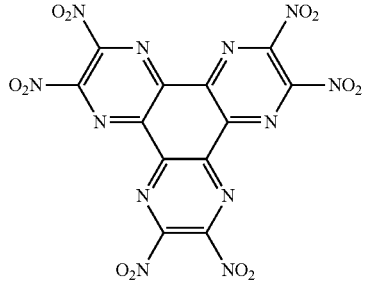

(4M)
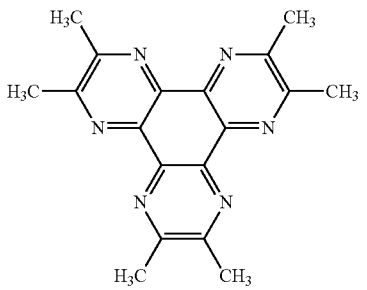

(4N)
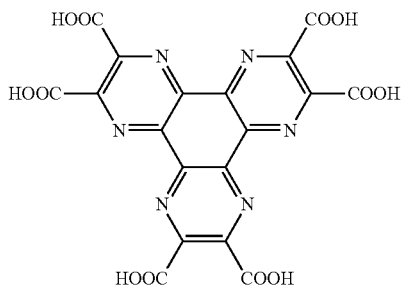

As an organic compound represented by the above general formula (1), besides the organic compounds represented by general formula (3), the organic compound in chemical formula 14 below represented by chemical formula (5A) wherein cycloalkane is formed by cyclobutane, and an organic compound represented by chemical formula (5B) wherein cycloalkane is formed by cyclooctane.

Chemical formula 14

(5A)
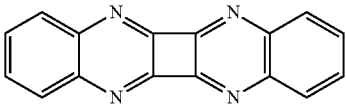

(5B)
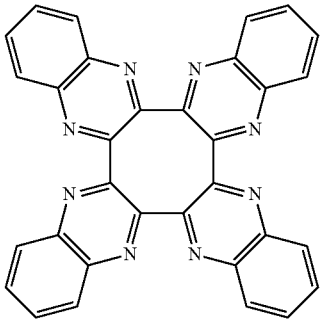

Further, as an organic compound having a cyclic one structure represented by general formula (2), organic compounds of chemical formula 15 and represented by chemical formulas (6A) to (6C) wherein cycloalkane is formed by cyclopentane, organic compounds represented by of chemical formula 16 and chemical formulas (7A) to (7C) wherein cycloalkane is formed by cycloheptane, and organic compounds of chemical formula 17 and represented by chemical formulas (8A) to (8C) wherein cycloalkane is formed by cyclohexane can be recited.

Chemical formula 15

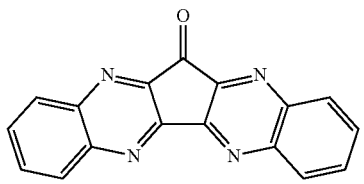
(6A)

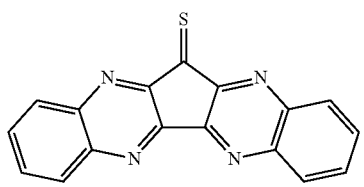
(6B)

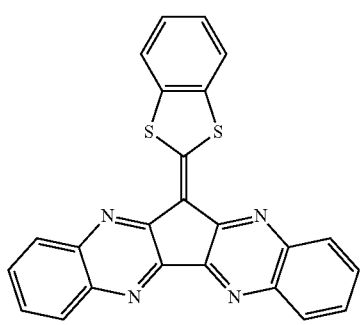
(6C)

Chemical formula 16

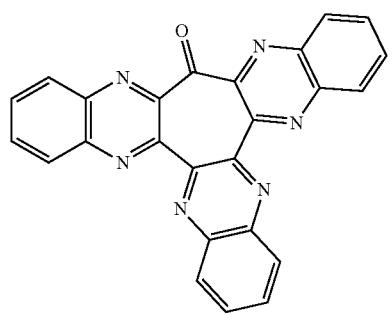
(7A)

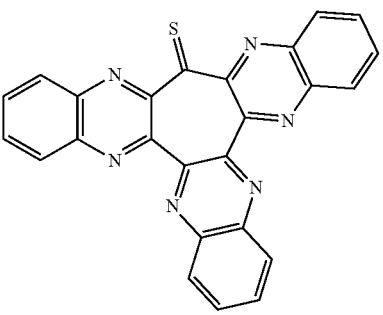
(7B)

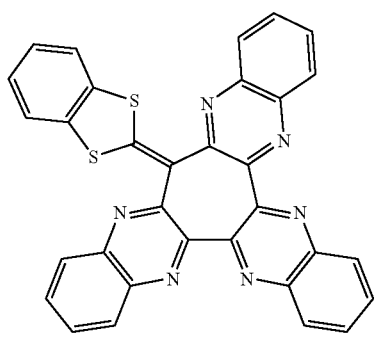
(7C)

Chemical formula 17

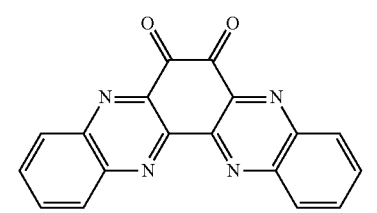
(8A)

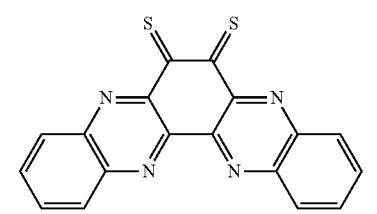
(8B)

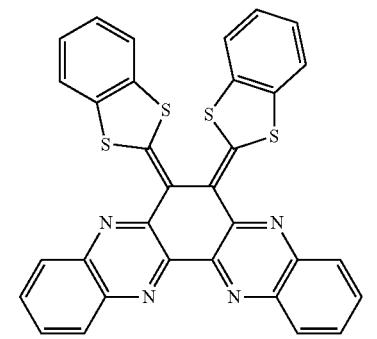
(8C)

The electrode active material generates a polyanion by electrochemical reduction reaction. Chemical reaction formula (9) shows one example of charging and discharging reaction expected when triquinoxalinylene represented by chemical formula (4A) is used as the electrode active material.

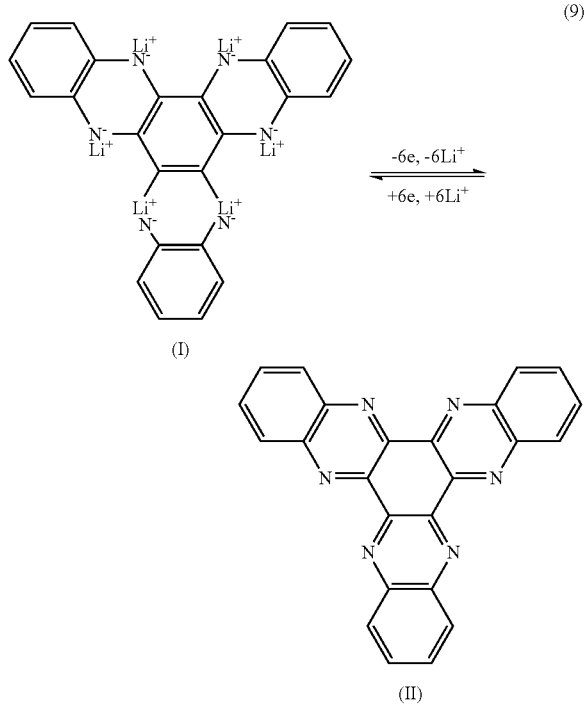

Since it is supposed that one molecule in triquinoxalinylene (II) reacts with six electrons to generate the polyanion represented by (I), the capacity density can be dramatically increased in comparison with the case of one-electron reaction.

While the molecular weight of the organic compound constituting the electrode active material is not particularly limited, the capacity accumulated per unit mass, namely the capacity density, will decrease as the part other than the pyrazine structure bound to cycloalkane such as cyclohexane enlarges. Therefore, as described above, it is preferred to select the molecular weight of the substituent within the range of up to about 250. When a polymer of an organic compound having a pyrazine structure bound to cycloalkane in the structural unit thereof is used, the molecular weight and molecular weight distribution are not particularly limited.

Next, a secondary battery in which the electrode active material is used will be described.

FIG. 1 is a section view showing a coin-shaped secondary battery as one embodiment of the secondary battery according to the present invention, and in the present embodiment, the electrode active material of the present invention is used as a cathode active material.

A battery can 1 has a cathode case 2 and an anode case 3, and cathode case 2 and anode case 3 each are formed into a disc-like thin sheet form. In the center of the bottom part of cathode case 2 constituting a cathode collector, a cathode 4 formed into a sheet from an electrode active material is disposed. Cathode 4 is overlaid with a separator 5 formed from a porous sheet or film such as microporous film, woven fabric, nonwoven fabric or the like, and further separator 5 is overlaid with an anode 6. As anode 6, for example, one obtained by overlapping metal foil of lithium on copper foil, or one obtained by applying a lithium storage material such as graphite or hard carbon on copper foil may be used. Anode 6 is overlaid with an anode collector 7 formed of metal, and on anode collector 7, a metallic spring 8 is placed. The interior space is filled with an electrolyte 9, and anode case 3 is fixed to cathode case 2 against the urging force of metallic spring 8, and sealed via a gasket 10.

Next, one example of a method for producing the secondary battery will be specifically described.

First, an electrode active material is formed into an electrode shape. For example, the electrode active material is mixed with a conductive assistant and a binder, and added with a solvent to prepare a slurry, and the slurry is applied on a cathode collector by an appropriate application method, and dried to form a cathode.

The conductive assistant is not particularly limited, and for example, carbonaceous microparticles such as graphite, carbon black and acetylene black, carbon fibers such as vapor-grown carbon fibers, carbon nanotube and carbon nanohorn, and conductive polymers such as polyaniline, polypyrrole, polythiophene, polyacetylene and polyacene, may be used. The conductive assistants may be used in combination of greater than or equal to two kinds. The content of the conductive assistant in cathode 4 is desirably 10 to 80% by mass.

Also, the binder is not particularly limited, and various resins such as polyethylene, polyvinylidene fluoride, polyhexafluoropropylene, polytetrafluoroethylene, polyethylene oxide and carboxymethyl cellulose, may be used.

The solvent is not particularly limited, and for example, basic solvents such as dimethyl sulfoxide, dimethyl formamide, 1-methyl-2-pyrrolidone, propylene carbonate, diethyl carbonate, dimethyl carbonate and γ-butyrolactone, nonaqueous solvents such as acetonitrile, tetrahydrofuran, nitrobenzene and acetone, protic solvents such as methanol and ethanol, and water. may be used.

The kind of the organic solvent, the blending ratio between the organic compound and the organic solvent, the kind of additive and the adding amount thereof and the like may be appropriately selected in consideration of the required characteristics, productivity and the like of the secondary battery. Then cathode 4 is impregnated with electrolyte 9 by soaking electrolyte 9 in cathode 4, and then cathode 4 is placed in the center of the bottom part of cathode case 2 constituting a cathode collector. The cathode 4 is overlaid with separator 5 impregnated with electrolyte 9, and further sequentially overlaid with anode 6 and anode collector 7, and then electrolyte 9 is injected into the interior space. Then, metallic spring 8 is placed on anode collector 7, gasket 10 is disposed in the circumference, anode case 3 is fixed to cathode case 2 by a caulker or the like to seal the exterior package, and thus a coin-shaped secondary battery is fabricated.

Electrolyte 9 is interposed between cathode (electrode active material) 4 and anode 6 that is an opposite electrode to mediate transportation of charged carriers between these electrodes. As such electrolyte 9, one having an ion conductivity of $10^{-5}$ to $10^{-1}$ S/cm at room temperature may be used, and for example, an electrolyte liquid prepared by dissolving an electrolyte salt in an organic solvent may be used.

As the electrolyte salt, for example, $LiPF_6$, $LiClO_4$, $LiBF_4$, $LiCF_3SO_3$, $LiC_2F_5SO_3$, $Li(CF_3SO_2)_2N$, $Li(C_2F_5SO_2)_2N$, $LiC(CF_3SO_2)_3$, $LiC(C_2F_5SO_2)_3$ and the like, may be used.

As the organic solvent, ethylene carbonate, propylene carbonate, dimethyl carbonate, diethyl carbonate, methylethyl carbonate, γ-butyrolactone, tetrahydrofuran, dioxolane, sulfolane, dimethyl formamide, dimethyl acetamide, 1-methyl-2-pyrrolidone and the like may be used.

Further, a solid electrolyte may be used as electrolyte 9. Examples of the polymer compounds used in the solid electrolyte include vinylidene fluoride polymers such as polyvinylidene fluoride, vinylidene fluoride-hexafluoropropylene copolymer, vinylidene fluoride-ethylene copolymer, vinylidene fluoride-monofluoroethylene copolymer, vinylidene fluoride-trifluoroethylene copolymer, vinylidene fluoride-tetrafluoroethylene copolymer and vinylidene fluoride-hexafluoropropylene-tetrafluoroethylene ternary copolymer, acrylonitrile polymers such as acrylonitrile-methylmethacrylate copolymer, acrylonitrile-methylacrylate copolymer, acrylonitrile-ethylmethacrylate copolymer, acrylonitrile-ethylacrylate copolymer, acrylonitrile-methacrylic acid copolymer, acrylonitrile-acrylic acid copolymer and acrylonitrile-vinyl acetate copolymer, and polyethylene oxide, ethylene oxide-propylene oxide copolymer, and polymers in the form of acrylate or methacrylate of these. Further, a gel that is obtained by immersing such a polymer compound with an electrolyte liquid may be used as electrolyte 9, or only the polymer compound containing an electrolyte salt may be directly used as electrolyte 9.

Since the electrode active material of the secondary battery is oxidized or reduced reversely by charging and discharging, it assumes different structures and states in the charged condition, the discharged condition or intermediate conditions thereof. In the present embodiment, the electrode active material is included in any one of a reaction starting substance (substance that brings chemical reaction in battery electrode reaction), a product (substance occurring as a result of chemical reaction), and an intermediate product at least in discharging reaction.

As described above, since the secondary battery is formed by using the electrode active material that undergoes multi-electron reaction according to the present embodiment, it is possible to obtain a secondary battery having large energy density and excellent stability.

The present invention is not limited to the above embodiment, and various modifications may be made without departing from the subject matter of the invention. For example, also the organic compound that mainly forms the electrode active material is not limited to the chemical formulas (4A) to (4N), (5A), (5B), (6A) to (6C), (7A) to (7C), (8A) to (8C) recited above which are just examples. In other words, as long as at least a pyrazine structure bound to cycloalkane is contained in the structural unit thereof, a battery electrode reaction that is generally identical to the chemical reaction formula (9) proceeds, and a desired secondary battery having large energy density and excellent stability can be obtained.

While a description was made for the coin-shaped secondary battery in the present embodiment, it goes without saying that the battery shape is not particularly limited, and the present invention may be applied to a cylinder type, a square type, a sheet type and so on. The exterior packaging method is not particularly limited, and a metal case, mold resin, aluminum laminate film or the like may be used.

Further, while the organic compound having a pyrazine structure bound to cycloalkane in the structural unit thereof is used as the cathode active material in the present embodiment, it may be advantageously used as an anode active material.

Next, examples of the present invention will be concretely described.

EXAMPLE 1

Synthesis of Organic Compound

According to the following synthesis scheme (A), triquinoxalinylene (4A) was synthesized.

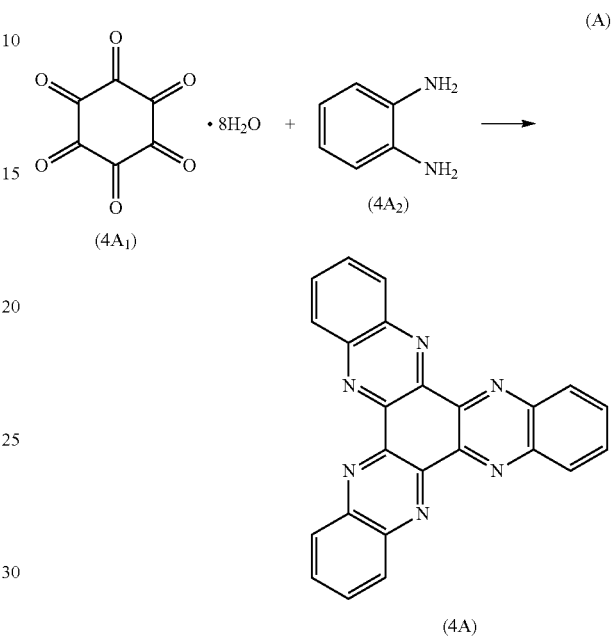

Specifically, 200 mg (0.6 mmol) of hexaketocyclohexane octahydrate ($A_1$), and 520 mg (4.5 mmol) of 1,2-phenylenediamine ($A_2$) were dissolved in 40 mL of acetic acid, and allowed to react under reflux for 24 hours. After filtering out the insoluble matter, the filtrate was combined with 50 mL of water and 50 mL of chloroform and phase-separated. The organic phase was concentrated, and the residue was purified by silica gel column chromatography (eluate: chloroform), to obtain 200 mg of triquinoxalinylene (4A) as a pale yellow solid.

Fabrication of Secondary Battery

Triquinoxalinylene (100 mg) synthesized in the manner as described above, 200 mg of graphite powder as a conductive assistant and 100 mg of polytetrafluoroethylene resin as a binder were weighed, and kneaded with mixing until the entirety was uniform, to obtain a mixture. Then the mixture was pressure-molded to fabricate a sheet-like member having a thickness of about 150 μm.

Next, the sheet-like member was dried in vacuo at 80° C. for one hour, and punched into a round of 12 mm in diameter, to fabricate a cathode (cathode active material) based on triquinoxalinylene. The cathode was impregnated with an electrolyte liquid by permitting the electrolyte liquid to soak in a void in the cathode. As the electrolyte liquid, an ethylene carbonate/diethyl carbonate mixed solution that is an organic solvent containing 1.0 mol/L by molar concentration of $LiPF_6$ (electrolyte salt) was used. The mixing ratio of ethylene carbonate/diethyl carbonate was ethylene carbonate:diethyl carbonate=3:7 by volume %.

Then, this cathode was placed on a cathode collector, and the cathode was overlaid with a separator having a thickness of 20 μm and formed from a polypropylene porous film impregnated with the electrolyte, and then the separator was overlaid with an anode formed of copper foil pasted with lithium on both faces.

After overlaying the anode with an anode collector made of Cu, an electrolyte liquid was injected into the interior space. Thereafter, a metallic spring was placed on the anode collector, and the anode case was joined with the cathode case in the condition that a gasket was disposed in the circumference, and the outer package was sealed by a caulker. In this manner, a hermetically-sealed coin-shaped battery having triquinoxalinylene as a cathode active material and metal lithium as an anode active material was fabricated.

Operation Check of Secondary Battery

The secondary battery fabricated in the manner described above was charged at a constant current of 0.1 mA to a voltage of 4.2 V, and then discharged at a constant current of 0.1 mA to 1.5 V. As a result, it was demonstrated that the secondary battery had two plateaus at 2.4 V and 1.5 V of charging and discharging voltage, and had a discharge capacity of 0.4 mAh. The capacity density per electrode active material calculated from this capacity was 420 Ah/kg.

The theoretical capacity density Q (Ah/kg) of the secondary battery is represented by Mathematical formula (1).

$$Q = \frac{1000 \times (Z \times 96500)}{3600 \times W} \quad (1)$$

Z represents the number of electrons involved in battery electrode reaction, and W represents the molecular weight of the electrode active material.

Since the molecular weight of triquinoxalinylene is 384.4, assuming that the number of electrons Z involved in battery electrode reaction is 6, the theoretical capacity density is 418 Ah/kg from Mathematical formula (1). That is, the capacity density obtained based on the actual measurement value of the discharge capacity approximately coincides with the theoretical capacity density, and hence it is confirmed that triquinoxalinylene is able to donate/receive six electrons per one molecule.

Thereafter, the secondary battery was subjected to repeated charging and discharging in the range of 4.0 to 1.5 V, and was able to keep greater than or equal to 80% of the initial capacity even after 10 cycles. This reveals that a stable secondary battery with little reduction in capacity after repeated charging and discharging can be obtained.

Also, the secondary battery fabricated in a similar manner was charged at a constant current of 0.1 mA to a voltage of 4.0 V, and retained for 168 hours while the voltage was applied, and then discharged at a constant current of 0.1 mA. As a result, the discharge capacity could be kept at greater than or equal to 80% although it was reduced in comparison with the case where discharging was conducted directly after charging. In other words, it was possible to obtain a stable secondary battery with little self-discharge.

EXAMPLE 2

Synthesis of Organic Compound

According to the following synthesis scheme (B), trifluorotriquinoxalinylene (4B) was synthesized.

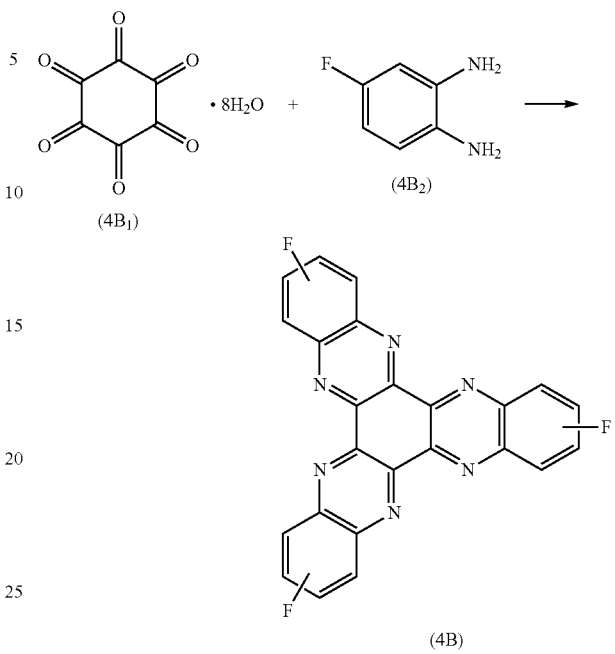

Hexaketocyclohexane octahydrate (4B$_1$) (200 mg (0.6 mmol)) and 568 mg (4.5 mmol) of 4-fluoro-1,2-phenylenediamine (4B$_2$) were dissolved in 40 mL of acetic acid, and allowed to react under reflux for 24 hours. After filtering out the insoluble matter, the filtrate was added with 50 mL of water and 50 mL of chloroform and phase-separated. The organic phase was concentrated, and the residue was purified by silica gel column chromatography (eluate: chloroform), to obtain 150 mg of trifluorotriquinoxalinylene (4B) as an ocher solid.

Fabrication of Secondary Battery

A secondary battery was fabricated in a similar manner as in Example 1 except that trifluorotriquinoxalinylene was used as a cathode active material.

Operation Check of Secondary Battery

The secondary battery fabricated in the manner as described above was charged at a constant current of 0.1 mA to a voltage of 4.2 V, and then discharged at a constant current of 0.1 mA to 1.5 V. As a result, it was demonstrated that the secondary battery had two plateaus at 2.5 V and 1.6 V of charging and discharging voltage, and had a discharge capacity of 0.32 mAh. The capacity density per electrode active material calculated from this capacity was 230 Ah/kg.

Since the molecular weight of trifluorotriquinoxalinylene is 438.4, assuming that the number of electrons Z involved in battery electrode reaction is 6, the theoretical capacity density is 366 Ah/kg from Mathematical formula (1). While the capacity density obtained based on the actual measurement value of the discharge capacity (=230 Ah/kg) is smaller than the theoretical capacity density (=366 Ah/kg), the theoretical capacity density is 183 Ah/kg when the number of electrons Z is 3. Accordingly, it was confirmed that trifluorotriquinoxalinylene undergoes multi-electron reaction in which at least greater than or equal to three electrons per one molecule are involved.

Thereafter, the secondary battery was subjected to repeated charging and discharging in the range of 4.2 to 1.5 V, and it was possible to keep greater than or equal to 80% of the initial capacity even after 10 cycles. This reveals that a stable secondary battery with little reduction in capacity after repeated charging and discharging can be obtained.

Also, the secondary battery fabricated in a similar manner was charged at a constant current of 0.1 mA to a voltage of 4.0 V, and retained for 168 hours while the voltage was applied, and then discharged at a constant current of 0.1 mA. As a result, the discharge capacity could be kept at greater than or equal to 80% although it was reduced in comparison with the case where discharging was conducted directly after charging. In other words, it was possible to obtain a stable secondary battery with little self-discharge.

EXAMPLE 3

Synthesis of Organic Compound

According to the following synthesis scheme (C), trichlorotriquinoxalinylene (4C) was synthesized.

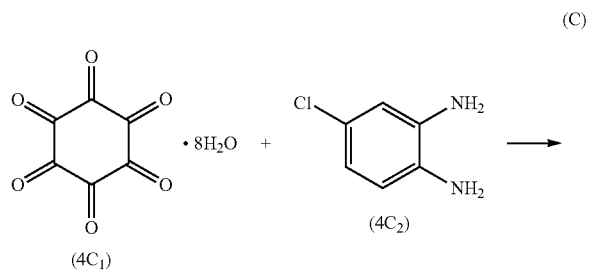

(4C)

Hexaketocyclohexane octahydrate (4C$_1$) (200 mg (0.6 mmol)) and 642 mg (4.5 mmol) of 4-chloro-1,2-phenylenediamine (4C$_2$) were dissolved in 40 mL of acetic acid, and allowed to react under reflux for 24 hours. After filtering out the insoluble matter, the filtrate was added with 50 mL of water and 50 mL of chloroform and phase-separated. The organic phase was concentrated, and the residue was purified by silica gel column chromatography (eluate: chloroform), to obtain 180 mg of trichlorotriquinoxalinylene (4C) as an ocher solid.

Fabrication of Secondary Battery

A secondary battery was fabricated in a similar manner as in Example 1 except that trichlorotriquinoxalinylene was used as a cathode active material.

Operation Check of Secondary Battery

The secondary battery fabricated in the manner as described above was charged at a constant current of 0.1 mA to a voltage of 4.2 V, and then discharged at a constant current of 0.1 mA to 1.5 V. As a result, it was demonstrated that the secondary battery had two plateaus at 2.4 V and 1.5 V of charging and discharging voltage, and had a discharge capacity of 0.42 mAh. The capacity density per electrode active material calculated from this capacity was 343 Ah/kg.

Since the molecular weight of trichlorotriquinoxalinylene is 487.7, assuming that the number of electrons Z involved in battery electrode reaction is 6, the theoretical capacity density is 330 Ah/kg from Mathematical formula (1). That is, the capacity density obtained based on the actual measurement value of the discharge capacity approximately coincides with the theoretical capacity density, and hence it is confirmed that trichlorotriquinoxalinylene is able to donate/receive six electrons per one molecule.

Thereafter, the secondary battery was subjected to repeated charging and discharging in the range of 4.2 to 1.5 V, and it was possible to keep greater than or equal to 80% of the initial capacity even after 10 cycles. This reveals that a stable secondary battery with little reduction in capacity after repeated charging and discharging can be obtained.

Also, the secondary battery fabricated in a similar manner was charged at a constant current of 0.1 mA to a voltage of 4.0 V, and retained for 168 hours while the voltage was applied, and then discharged at a constant current of 0.1 mA. As a result, the discharge capacity could be kept at greater than or equal to 80% although it was reduced in comparison with the case where discharging was conducted directly after charging. In other words, it was possible to obtain a stable secondary battery with little self-discharge.

EXAMPLE 4

Synthesis of Organic Compound

According to the following synthesis scheme (D), tribromotriquinoxalinylene (4D) was synthesized.

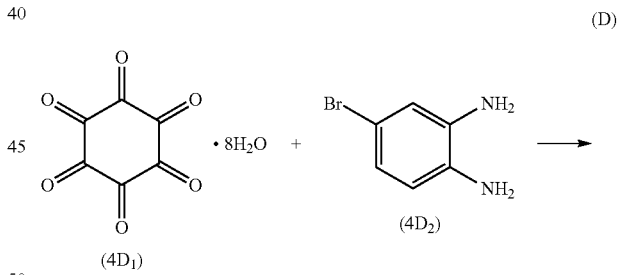

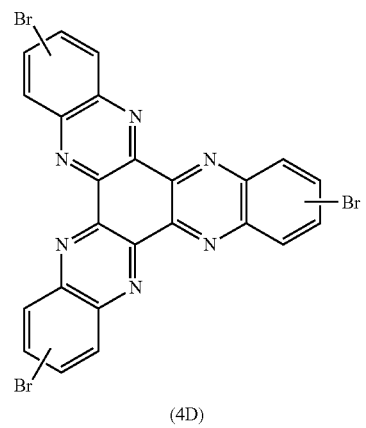

(4D)

Hexaketocyclohexane octahydrate (4D$_1$) (200 mg (0.6 mmol)) and 841 mg (4.5 mmol) of 4-bromo-1,2-phenylenediamine (4D$_2$) were dissolved in 40 mL of acetic acid, and allowed to react under reflux for 24 hours. After filtering out the insoluble matter, the filtrate was added with 50 mL of water and 50 mL of chloroform and phase-separated. The organic phase was concentrated, and the residue was purified by silica gel column chromatography (eluate: chloroform), to obtain 230 mg of tribromotriquinoxalinylene (4D) as a dark brown solid.

Fabrication of Secondary Battery

A secondary battery was fabricated in a similar manner as in Example 1 except that tribromotriquinoxalinylene was used as a cathode active material.

Operation Check of Secondary Battery

The secondary battery fabricated in the manner as described above was charged at a constant current of 0.1 mA to a voltage of 4.2 V, and then discharged at a constant current of 0.1 mA to 1.5 V. As a result, it was demonstrated that the secondary battery had two plateaus at 2.5 V and 1.8 V of charging and discharging voltage, and had a discharge capacity of 0.35 mAh. The capacity density per electrode active material calculated from this capacity was 260 Ah/kg.

Since the molecular weight of tribromotriquinoxalinylene is 621.1, assuming that the number of electrons Z involved in battery electrode reaction is 6, the theoretical capacity density is 258 Ah/kg from Mathematical formula (1). That is, the capacity density obtained based on the actual measurement value of the discharge capacity approximately coincides with the theoretical capacity density, and hence it is confirmed that tribromotriquinoxalinylene is able to donate/receive six electrons per one molecule.

Thereafter, the secondary battery was subjected to repeated charging and discharging in the range of 4.2 to 1.5 V, and it was possible to keep greater than or equal to 80% of the initial capacity even after 10 cycles. This reveals that a stable secondary battery with little reduction in capacity after repeated charging and discharging can be obtained.

Also, the secondary battery fabricated in a similar manner was charged at a constant current of 0.1 mA to a voltage of 4.0 V, and retained for 168 hours while the voltage was applied, and then discharged at a constant current of 0.1 mA. As a result, the discharge capacity could be kept at greater than or equal to 80% although it was reduced in comparison with the case where discharging was conducted directly after charging. In other words, it was possible to obtain a stable secondary battery with little self-discharge.

EXAMPLE 5

Synthesis of Organic Compound

According to the following synthesis scheme (E), trimethyltriquinoxalinylene (4H) was synthesized.

(E)

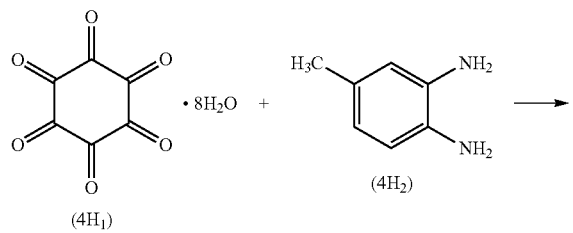

(4H$_1$) (4H$_2$)

-continued

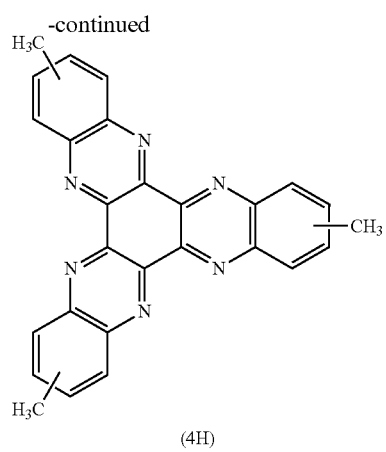

(4H)

Hexaketocyclohexane octahydrate (4H$_1$) (200 mg (0.6 mmol)) and 550 mg (4.5 mmol) of 4-methyl-1,2-phenylenediamine (4H$_2$) were dissolved in 40 mL of acetic acid, and allowed to react under reflux for 24 hours. After filtering out the insoluble matter, the filtrate was added with 50 mL of water and 50 mL of chloroform and phase-separated. The organic phase was concentrated, and the residue was purified by silica gel column chromatography (eluate: chloroform), to obtain 110 mg of trimethyltriquinoxalinylene (4H) as an orange solid.

Fabrication of Secondary Battery

A secondary battery was fabricated in a similar manner as in Example 1 except that trimethyltriquinoxalinylene was used as a cathode active material.

Operation Check of Secondary Battery

The secondary battery fabricated in the manner as described above was charged at a constant current of 0.1 mA to a voltage of 4.2 V, and then discharged at a constant current of 0.1 mA to 1.5 V. As a result, it was demonstrated that the secondary battery had three plateaus at 2.5 V, 2.0 V and 1.5 V of charging and discharging voltage, and had a discharge capacity of 0.28 mAh. The capacity density per electrode active material calculated from this capacity was 200 Ah/kg.

Since the molecular weight of trimethyltriquinoxalinylene is 426.5, the theoretical capacity density is 375 Ah/kg from Mathematical formula (1). While the capacity density obtained based on the actual measurement value of the discharge capacity (=200 Ah/kg) is smaller than the theoretical capacity density (=375 Ah/kg), the theoretical capacity density is 189 Ah/kg when the number of electrons Z is 3. Accordingly, it was confirmed that trimethyltriquinoxalinylene undergoes multi-electron reaction in which at least greater than or equal to three electrons per one molecule are involved.

Thereafter, the secondary battery was subjected to repeated charging and discharging in the range of 4.2 to 1.5 V, and it was possible to keep greater than or equal to 80% of the initial capacity even after 10 cycles. This reveals that a stable secondary battery with little reduction in capacity after repeated charging and discharging can be obtained.

Also, the secondary battery fabricated in a similar manner was charged at a constant current of 0.1 mA to a voltage of 4.0 V, and retained for 168 hours while the voltage was applied, and then discharged at a constant current of 0.1 mA. As a result, the discharge capacity could be kept at greater than or equal to 80% although it was reduced in comparison with the case where discharging was conducted directly after charging. In other words, it was possible to obtain a stable secondary battery with little self-discharge.

EXAMPLE 6

Synthesis of Organic Compound

According to the following synthesis scheme (F), tribenzoyltriquinoxalinylene (4J) was synthesized.

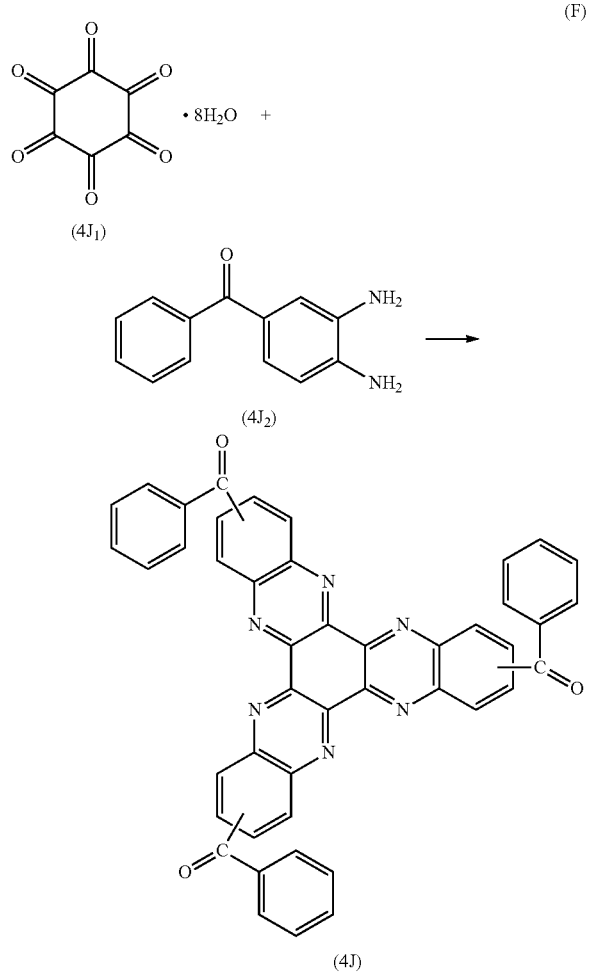

Hexaketocyclohexane octahydrate (4J$_1$) (200 mg (0.6 mmol)) and 955 mg (4.5 mmol) of 3,4-diaminobenzophenone (4J$_2$) were dissolved in 40 mL of acetic acid, and allowed to react under reflux for 24 hours. After filtering out the insoluble matter, the filtrate was added with 50 mL of water and 50 mL of chloroform and phase-separated. The organic phase was concentrated, and the residue was purified by silica gel column chromatography (eluate: chloroform), to obtain 250 mg of tribenzoyltriquinoxalinylene (4J) as a yellowish brown solid.

Fabrication of Secondary Battery

A secondary battery was fabricated in a similar manner as in Example 1 except that tribenzoyltriquinoxalinylene was used as a cathode active material.

Operation Check of Secondary Battery

The secondary battery fabricated in the manner as described above was charged at a constant current of 0.1 mA to a voltage of 4.2 V, and then discharged at a constant current of 0.1 mA to 1.5 V. As a result, it was demonstrated that the secondary battery had two plateaus at 2.5 V and 1.5 V of charging and discharging voltage, and had a discharge capacity of 0.26 mAh. The capacity density per electrode active material calculated from this capacity was 240 Ah/kg.

On the other hand, since the molecular weight of tribenzoyltriquinoxalinylene is 696.7, assuming that the number of electrons Z involved in battery electrode reaction is 6, the theoretical capacity density is 231 Ah/kg from Mathematical formula (1). That is, the capacity density obtained based on the actual measurement value of the discharge capacity approximately coincides with the theoretical capacity density, and hence it is confirmed that tribenzoyltriquinoxalinylene is able to donate/receive six electrons per one molecule.

Thereafter, the secondary battery was subjected to repeated charging and discharging in the range of 4.2 to 1.5 V, and it was possible to keep greater than or equal to 80% of the initial capacity even after 10 cycles. This reveals that a stable secondary battery with little reduction in capacity after repeated charging and discharging can be obtained.

Also, the secondary battery fabricated in a similar manner was charged at a constant current of 0.1 mA to a voltage of 4.0 V, and retained for 168 hours while the voltage was applied, and then discharged at a constant current of 0.1 mA. As a result, the discharge capacity could be kept at greater than or equal to 80% although it was reduced in comparison with the case where discharging was conducted directly after charging. In other words, it was possible to obtain a stable secondary battery with little self-discharge.

INDUSTRIAL APPLICABILITY

A stable secondary battery having large energy density, outputting high power, and having excellent cycle characteristics with little reduction in capacity even after repetition of charging and discharging is realized.

REFERENCE SIGNS LIST

4 cathode
6 anode
9 electrolyte

The invention claimed is:

1. An electrode active material used as an active material in a secondary battery that is repeatedly charged and discharged by battery electrode reaction, comprising an organic compound containing a pyrazine structure bound to cycloalkane in the structural unit thereof.

2. The electrode active material according to claim 1, wherein said organic compound is represented by the general formula:

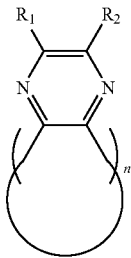

in which R$_1$ and R$_2$ individually represent at least one member of the group consisting of a hydrogen atom, a substituted or unsubstituted C$_1$-C$_{50}$ alkyl group, an aryl group, an aralkyl group, a cycloalkyl group, an alkoxyl group, an alkenyl group, an aryloxy group, an arylamino group, an alkylamino group, a thioaryl group, a thioalkyl group, a heterocyclic group, a formyl group, a silyl group, a boryl group, a stannyl group, a cyano group, a nitro group, a nitroso group, a carboxyl group, an alkoxycarbonyl group and a halogen atom, and $R_1$ and $R_2$ may be bound to each other to form a saturated or unsaturated ring, and n is an integer of 1 to 50.

3. The electrode active material according to claim 2, in which $R_1$ and $R_2$ have a total combined molecular weight of up to about 250.

4. The electrode active material according to claim 1 which is selected from the group consisting of (4A)
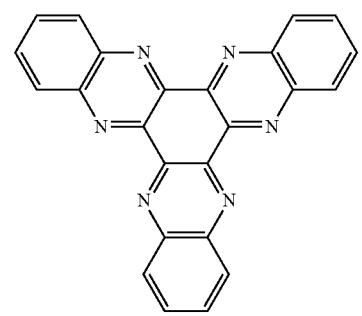

(4B)
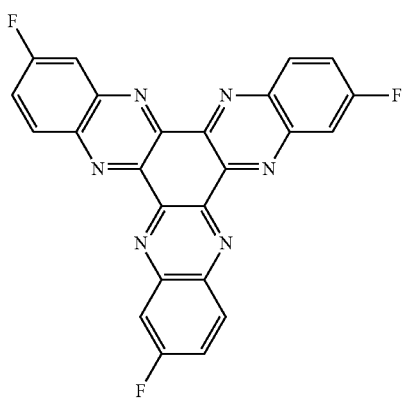

(4C)
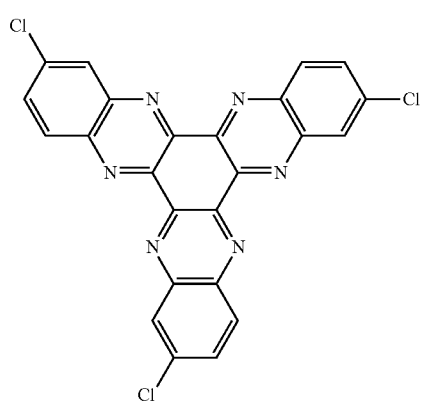

(4D)
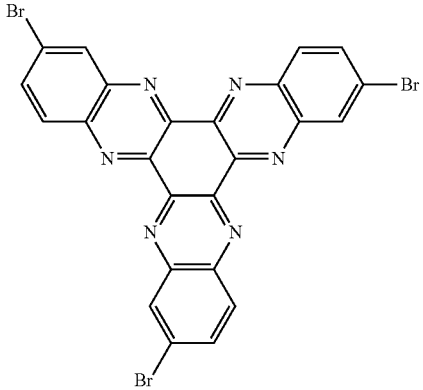

(4H)
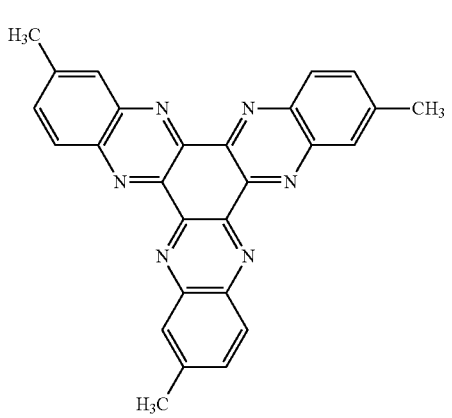

(4J)
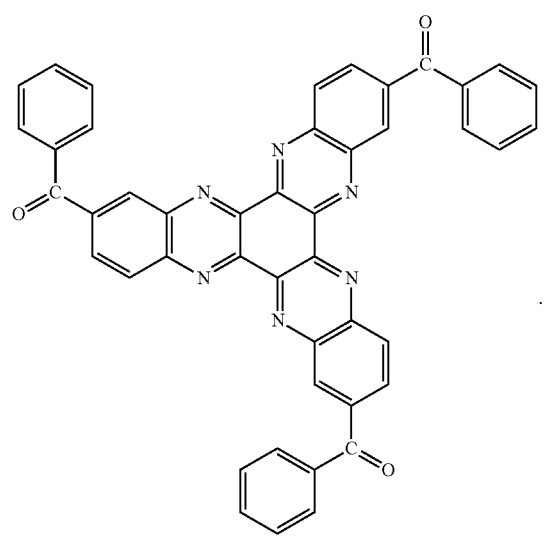

5. The electrode active material according to claim 1 which is selected from the group consisting of

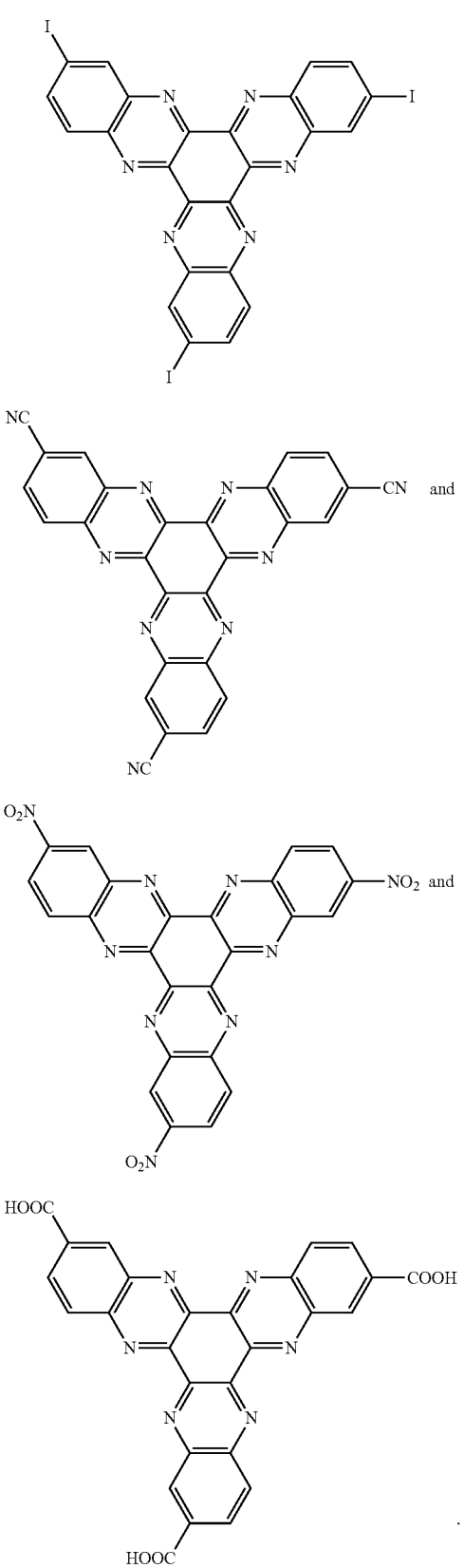

6. The electrode active material according to claim 1, wherein said organic compound is represented by the general formula:

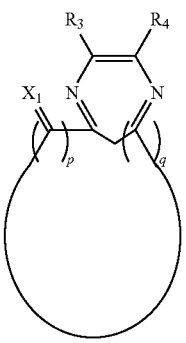

in which $R_3$ and $R_4$ individually represent at least one member of the group consisting of a hydrogen atom, a substituted or unsubstituted $C_1$-$C_{50}$ alkyl group, an aryl group, an aralkyl group, a cycloalkyl group, an alkoxyl group, an alkenyl group, an aryloxy group, an arylamino group, an alkylamino group, a thioaryl group, a thioalkyl group, a heterocyclic group, a formyl group, a silyl group, a boryl group, a stannyl group, a cyano group, a nitro group, a nitroso group, a carboxyl group, an alkoxycarbonyl group and a halogen atom; $X_1$ represents $CH_2$, $CF_2$, O, S, Se, N—R', P—R', and As—R' in which R' represents at least one member of the group consisting of a hydrogen atom, a substituted or unsubstituted C1-C50 alkyl group, an aryl group, an aralkyl group, a cycloalkyl group, an alkoxyl group, an alkenyl group, an aryloxy group, an arylamino group, an alkylamino group, a thioaryl group, a thioalkyl group, a heterocyclic group, a silyl group, a boryl group, a stannyl group, a cyano group, a nitro group, a nitroso group, and a halogen atom, and $R_3$, $R_4$ and $X_1$ may be bound to each other to form a saturated or unsaturated ring; and p and q are individually an integer of 1 to 50.

7. The electrode active material according to claim 1, wherein said organic compound is represented by the general formula:
and

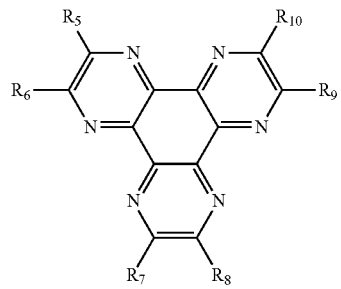

in which $R_5$ to $R_{10}$ individually represent at least one member of the group consisting of a hydrogen atom, a substituted or unsubstituted C1-C50 alkyl group, an aryl group, an aralkyl group, a cycloalkyl group, an alkoxyl group, an alkenyl group, an aryloxy group, an arylamino group, an alkylamino group, a thioaryl group, a thioalkyl group, a heterocyclic group, a formyl group, a silyl group, a boryl group, a stannyl group, a cyano group, a nitro group, a nitroso group, a carboxyl group, an alkoxycarbonyl group and a halogen atom, and may be bound to each other to form a saturated or unsaturated ring.

8. A secondary battery wherein the electrode active material according to claim 7 is present in at least one of a reaction starting substance, a product and an intermediate product during the discharging reaction of battery electrode reaction.

9. A secondary battery wherein the electrode active material according to claim 6 is present in at least one of a reaction starting substance, a product and an intermediate product during the discharging reaction of battery electrode reaction.

10. A secondary battery wherein the electrode active material according to claim 5 is present in at least one of a reaction starting substance, a product and an intermediate product during the discharging reaction of battery electrode reaction.

11. A secondary battery wherein the electrode active material according to claim 4 is present in at least one of a reaction starting substance, a product and an intermediate product during the discharging reaction of battery electrode reaction.

12. A secondary battery wherein the electrode active material according to claim 3 is present in at least one of a reaction starting substance, a product and an intermediate product during the discharging reaction of battery electrode reaction.

13. A secondary battery wherein the electrode active material according to claim 2 is present in at least one of a reaction starting substance, a product and an intermediate product during the discharging reaction of battery electrode reaction.

14. A secondary battery wherein the electrode active material according to claim 1 is present in at least one of a reaction starting substance, a product and an intermediate product during the discharging reaction of battery electrode reaction.

15. A secondary battery comprising a cathode, an anode, and an electrolyte, wherein said cathode comprises the electrode active material according to claim 1.

16. A secondary battery comprising a cathode, an anode, and an electrolyte, wherein said cathode comprises the electrode active material according to claim 2.

17. A secondary battery comprising a cathode, an anode, and an electrolyte, wherein said cathode comprises the electrode active material according to claim 3.

18. A secondary battery comprising a cathode, an anode, and an electrolyte, wherein said cathode comprises the electrode active material according to claim 6.

19. A secondary battery comprising a cathode, an anode, and an electrolyte, wherein said cathode comprises the electrode active material according to claim 7.

* * * * *